United States Patent [19]

Viza

[11] 4,316,962
[45] Feb. 23, 1982

[54] NOVEL CELL LINE

[75] Inventor: Dimitri Viza, Bourg-la-Reine, France

[73] Assignee: The International Institute of Differentiation Limited, Guernsey, Channel Islands

[21] Appl. No.: 860,439

[22] Filed: Dec. 14, 1977

[30] Foreign Application Priority Data

Dec. 16, 1976 [GB] United Kingdom ............... 52675/76

[51] Int. Cl.³ ............................................... C12N 5/02
[52] U.S. Cl. .................................................. 435/241
[58] Field of Search ......................... 195/1.8; 435/241

[56] References Cited

PUBLICATIONS

Moore et al., Cancer, vol. 19, No. 5 (May 1966), pp. 713–723.
Minowada et al., J. Nat. Can. Inst., vol. 49, No. 3, Sep. 1972, pp. 891–895.
Nilsson, Int. J. Cancer, vol. 7 (1971), pp. 380–396.
Paul, Cell & Tiss. Cult., Fift. Edit. 1975, pp. 25–39, 62, 63, 232–235, 466–470.
Slesinger et al., Chromosoma (Berl.), vol. 49 (1974), pp. 173–184.
Abercrombie et al., A Dictionary of Biology–Sixth Edit. (Penguin Books), pp. 110–111.
Moorhead et al., Experiment. Cell. Res., vol. 20 (1960), pp. 613–616.
Nilsson et al., Int. J. Cancer, vol. 8 (1971), pp. 443–450.
Moore, Methods in Cancer Res., Chap. X (1970), pp. 423–453.
Collins et al., Nature, vol. 270, Nov. 24, 1977, pp. 347–349.
Moore et al., J. Sur. Res. vol. 5, No. 6 (1965), pp. 270–282.
Zimmerman, Experiment Cell Res., vol. 20, pp. 540–547.
Schlesinger et al., Chem. Abst., vol. 82 (1975), pp. 122425f.
Slezinger et al., Chem. Abst., vol. 81 (1974), pp. 102410y.
Baumal et al., Nature New Biology, vol. 230 (Mar. 3, 1971), pp. 20–21.
Paltrowitz et al., Sinai Journ., vol. 38 (1971), pp. 284–292.
Moore et al., J.A.M.A., vol. 199, No. 8, Feb. 20, 1967, pp. 519–524.
Imamura et al., PSEBM, vol. 128 (1968), pp. 1179–1183.

*Primary Examiner*—Sam Rosen
*Attorney, Agent, or Firm*—Stevens, Davis, Miller & Mosher

[57] ABSTRACT

A cell line, identified by the reference LDV/7, was established from peripheral blood leucocytes of a 75 year old male volunteer, and may be propagated by culturing the cells in a suitable nutrient culture medium. The cell line may be used in the production of immunological material.

8 Claims, No Drawings

NOVEL CELL LINE

This invention relates to cell lines which may be used for the production of immunological material.

The development of new cell lines which can be continuously subcultured is an area of research which has been the subject of a considerable amount of activity in recent years. Such cell lines offer substantial advantages over primary cultures in several fields of microbiology. For example, they are of great use to virologists both in experimental work and in the cultivation of viruses for vaccine production. For example, British Patent Specification No. 1,015,262 describes and claims the cell line known generally by the reference BHK 21 which has been developed in conjunction with such virus cultures.

During the past decade the efforts of several laboratories have been directed towards establishing a cell line derived from human peripheral blood leucocytes. Several such cell lines including lines derived from lymphoblastoid cells (formative leucocyte cells), have been established by various research groups. For example, see Nilsson, K., et al, Int. J. Cancer, Vol. 3, pp. 183-190, 1968, "Development of Immunocytes and Immunoglobulins, Production in Long Term Cultures from Normal and Malignant Human Lymph Nodes"; and Moore, G. E. et al, J. of Amer. Med. Assoc., Vol. 199, 8, pp. 87-92, 1967, "Culture of Normal Human Leukocytes".

A new cell line has now been developed, which can be propagated without showing any substantial change in character, based on peripheral blood leucocytes obtained from a 75 year old, apparently healthy, male volunteer. This cell line has been designated LDV/7. The cells of this line have been found to be capable of producing specific immunological material, for example specific antibodies and immune RNA. The cells can be grown in suspension cultures, either in static cultures or spinner cultures, but they can also be cultivated in agar. This property is particularly useful since it enables well established bacteriological methods to be applied to the in vitro control of human cells. Cloning is possible for example, and it is also possible to study the effect of various factors, such as colony stimulating factor, on the differentiation of the cells.

Accordingly, the present invention provides a cell culture system comprising cells of the cell line identified by the reference LDV/7 in a nutrient culture medium therefor.

The present invention also provides a process for the propagation of cells of the cell line identified by the reference LDV/7, which comprises culturing the cells in a nutrient culture medium therefor.

The cell line was initially established by the following procedure (the percentages referred to throughout the specification being by volume:

Most of the erythrocytes were separated from the original blood sample by the addition of 20% Plaspagel R, and discarded after sedimentation in test tubes. The recovered suspension contained a ratio of erythrocytes to leucocytes of less than 20:1. The leucocytes thus recovered were then suspended in RPMI 1640 medium, (see Journal of American Medical Association, volume 199, 8, p. 87) containing 20% foetal calf serum, at a concentration of $2 \times 10^6$ leucocytes/ml. Two thirds of the medium was replaced by fresh medium twice a week. Since cell death occurred within the first weeks, the cultures were concentrated as required in order to keep the cell concentration above $10^6$ cells/ml.

The cells were cultured in glass Roux bottles. Six weeks after the start of the cultures the cells in one of these bottles showed growth characteristics, i.e., they became larger and started multiplying and these were used to initially set up the LDV/7 cell line.

This cell line has since been grown in large quantities, using the propagation techniques described below:

The LDV/7 cell line can be maintained in a variety of nutrient media. It can be cultivated in RPMI 1640 medium containing from 5% to 30% foetal calf serum. Preferably, the nutrient medium consists of RPMI medium containing 10% foetal calf serum. Additionally, McCoy's and Eagle's Essential Medium may be used in subculturing the cell line.

The cells grow in suspension at 37° C., and form clumps which can be dispersed by gentle agitation of the medium. The cells are passaged at least twice a week. The usual seeding number is $5 \times 10^5$ cells/ml and the cells are allowed to grow in static culture until a concentration of $10^6$ cells/ml is reached. The cells will also grow in spinner culture in which a rotating, sterile magnetic stirrer keeps the cells in suspension in the nutrient medium. A higher concentration of the order of $1.5 \times 10^6$ cells/ml can then be obtained before subculturing the cells. The percentage of dead cells is roughly of the order of 5%, but varies according to culture conditions. The generation time of the cells is approximately 24 hours, again depending on the culture conditions.

In general, the conditions such as pH and temperature under which the cell line is propagated are substantially the same as those which leucocytes would encounter in a human being.

Karyotype analysis of the cells showed that the LDV/7 cell line is hypotetraploid. The number of chromosomes varies between 80 and 93. A study of the morphology of the cells under the light microscope revealed a heterogeneous cell size and that most of the cells have a blast-like appearance. Further work using an electron microscope confirmed the heterogeneity of the cell line, showing round mononuclear cells of varying size with cytoplasmic differentiation and rough endoplasmic reticulum, and macrophagic properties. These appear to be at least two cell populations, one of small cells of less than 15μm diameter, and one of large cells of from 15-30 μm diameter. Apparently the large cells derive from the small ones.

Three clones have been obtained with chromosome numbers of 84 for the first and 85 for the second and third, thus attesting cloning efficiency.

The phagocytic properties of the cells were also studied under the electron microscope. Some of the cells could clearly be seen to be phagocytised by other cells. No viral particles were discovered in the electron micrographs obtained, either from samples taken under the usual culture conditions or from culture grown at +40° C. It is worth noting that this cell line is very sensitive to the adrenal cortical steroid hormone cortisone, suggesting the presence of lymphoblastoid cells and/or stem cells. It is also worth noting that no EB virus antigens were selected by immunofluorescence.

Tissue typing of the LDV/7 cells for histo-compatibility HL-A antigens revealed the presence of the following specificites: HLA 2 and HLA 32 for the first locus, and HLA specificity W 14 for the second locus. However, weak reactivity with other antisera for other HLA specificities was also observed, but this was considered non-specific.

The LDV/7 cell line has been extensively studied in conjunction with experiments concerning the production of immunological material. It was discovered that the LDV/7 cells can be induced by nucleic acids (RNA and DNA) derived from lymphoid organs of animals immunised with specific antigens. After induction, the cells were shown to be able to replicate the nucleic acids used for their induction. It was found that these replicated nucleic acids retained their antigenic specificity. Furthermore, it was shown that dialysates derived from the LDV/7 cells induced with nucleic acids for a specific antigen will transfer the cellular immunity against these antigens when injected in vivo into human recipients.

Conversely, it was shown that cell dialysates obtained from human or animal lymphoid cells sensitized to a given antigen, as well as from induced LDV/7 cells were able to induce "naive" LDV/7 cells to produce nucleic acids which were able to transfer immune reactivity specifically for those antigens. It was further discovered that the LDV/7 cells, after induction with these "immune" nucleic acids, and/or cell dialysates, would produce antibodies specific to the antigens against which the lymphoid cells producing the immune nucleic acids or the immune cell dialysates were sensitized. Antibodies were recovered from the supernatants of these cultures, but in addition these supernatants contained material which could be used to induce "naive" lymphoid cells to produce immune nucleic acids and immune cell dialysates for the same antigenic specificity against which the cells producing the supernatants were sensitized. The production of the immunological material described above is also described, and is claimed, in copending application Ser. No. 860,451 filed on even date herewith, now U.S. Pat. No. 4,224,404.

LDV/7 cells have been deposited at the Laboratoire d'Immonobiologie, Faculté de Médecine Broussais Hôtel-Dieu, 15, rue de l'Ecole de Médecine, Paris 75006, and are available to the public on request.

I claim:

1. A cell culture system comprising cells of the cell line identified by the reference LDV/7 in a synthetic nutrient culture medium therefor.

2. A cell culture system according to claim 1, in which the nutrient culture medium for the suspension culture is RPMI 1640 medium containing from 5% to 30% foetal calf serum.

3. A cell culture system according to claim 2, in which 10% foetal calf serum is present in the RPMI 1640 medium.

4. A cell culture system according to claim 1, in which the nutrient culture medium for the suspension culture is McCoy's or Eagle's Essential Medium.

5. A process for the propagation of cells of the cell line identified by the reference LDV/7, which comprises culturing the cells in a synthetic nutrient culture medium therefor.

6. A process according to claim 5, in which the nutrient culture medium for the suspension culture is RPMI 1640 medium containing from 5% to 30% foetal calf serum.

7. A process according to claim 6, in which 10% foetal calf serum is present.

8. A process according to claim 5, in which the nutrient culture medium for the suspension culture is McCoy's or Eagle's Essential Medium.

* * * * *